United States Patent [19]
Jeshuran

[11] Patent Number: 5,197,463
[45] Date of Patent: Mar. 30, 1993

[54] SINGLE STAGE SEAL ADAPTOR FOR ENDOTRACHEAL INTUBATION AND REMOVAL OF ANESTHESIA MASK

[76] Inventor: Winston R. Jeshuran, 615 Riverside Dr., Cheshire, Conn. 06410

[21] Appl. No.: 805,290

[22] Filed: Dec. 10, 1991

[51] Int. Cl.⁵ .......................................... A61M 16/00
[52] U.S. Cl. ............................... 128/207.14; 128/912; 128/206.28; 604/256; 604/905; 277/216
[58] Field of Search ...................... 128/207.14, 207.15, 128/207.16, 207.17, 205.25, 634, 911, 912, 202.28, 203.29, 206.29, 206.28, 208.26, DIG. 26; 604/43, 175, 176, 167, 244, 256, 148, 161, 205, 905; 285/108; 277/216, 217

[56] References Cited

U.S. PATENT DOCUMENTS

| | | | |
|---|---|---|---|
| 4,430,081 | 2/1984 | Timmermans | 604/256 |
| 4,432,759 | 2/1984 | Gross et al. | 604/905 X |
| 4,580,556 | 4/1986 | Kondur | 128/206.28 |
| 4,673,393 | 6/1987 | Suzuki et al. | 604/167 |

Primary Examiner—V. Millin
Assistant Examiner—William M. Pierce
Attorney, Agent, or Firm—Robert A. Seemann

[57] ABSTRACT

An adaptor for delivering a tube to a patient by way of the adaptor and an anesthesia mask includes a compressable seal core of separable sections which define a passageway for the tube when the sections are assembled. A body and a head of the adaptor include seats for receiving the seal core with the passageway oriented for delivering the tube through the adaptor by way of an opening in the head. The seal core is adjustably compressed by the seats to form an adjustable seal around the tube. The openings in the head and body of the adaptor for the tube are larger in diameter than the back of the tube, and can be removed completely from the tube over the back end of the tube.

5 Claims, 6 Drawing Sheets

SINGLE STAGE SEAL ADAPTOR FOR ENDOTRACHEAL INTUBATION AND REMOVAL OF ANESTHESIA MASK

BACKGROUND OF THE INVENTION

1. Field of the Invention

This invention relates to a respiratory device and method, more particularly to an adaptor for introducing an endoscope and endotracheal tube to an anesthesia mask, for nasal or oral intubation, by way of a single stage seal, and for removal of the mask and adaptor from the endotracheal tube.

2. Description of the Prior Art

Endotracheal intubation is now the standard and accepted method for administering general anesthesia for major surgical procedures. It provides good airway control, making general anesthesia safer.

Certain patients classified as "The Difficult Intubation" present themselves from time to time. They include those with limited cervical spine mobility, poor mobility of the mandible, a receding lower jaw with obtuse mandibular angle, short muscular neck, high arched palate associated with a long narrow mouth, and protruding upper incisors. An anesthesiologist may then resort to the flexible fiberoptic scope to provide a coaxial guide for the endotracheal tube.

During this procedure one wishes to have equipment which permits easy, quick, yet gentle and controlled insertion of the fiberoptic scope, then of the endotracheal tube, with minimum break in ventilation time or loss of ventilation pressure.

The present invention satisfies that need and also permits complete removal of the mask and associated anesthesia circuit connectors from the scope and tube systems when the tube is in place for ventilating the patient.

Various devices and methods have been developed over the years to facilitate fiber optic endotracheal intubation. Many methods use a mask with an adaptor for receiving and delivering the fiberscope and endotracheal tube to the mask, and a connector on the mask or on the adaptor for delivering anesthesia to the mask.

Steps embodied in various methods for fiber optic endotracheal intubation typically include:

Method A

After inducing general anesthesia by mask, remove the mask and:

1. insert an airway for tongue control
2. insert a fiber optic scope by way of nose or mouth and optically guide the fiber optic scope into the trachea, slip an endotracheal tube which was resident over the back portion of the fiberoptic scope, in over the fiberoptic scope until it locates in the trachea, withdraw the fiber optic scope from the endotracheal tube, inflate the endotracheal tube cuff.
3. apply gas supply to the endotracheal tube Method B 1. insert an airway
2. apply a mask having a diaphragmed opening in the mask or in an adaptor attached to the mask, and another anesthetic circuit opening.
3. attach anesthetic gas supply to the circuit opening,
4. insert an endotracheal tube containing a fiberoptic scope, through the diaphragm opening, into the mask, and optically guide the fiber optic scope by way of the nose or mouth into the trachea, follow with the endotracheal tube, moving it in over the fiberoptic scope until it locates in the trachea, withdraw the fiber optic scope from the endotracheal tube, inflate the endotracheal tube cuff.
5. apply gas supply to the endotracheal tube and disconnect anesthesia circuit from the circuit opening.
6. slide the mask and adaptor back along the endotracheal tube to remove it from the face, and hang the mask and tube clear of the immediate work area.

7-9. alternate to hanging the mask;

7. remove the gas supply from the rear end of the endotracheal tube, and remove the coupler from the endotracheal tube,
8. slip the mask and adaptor off the endotracheal tube,
9. reinstall the coupler and the gas supply.

Method C

After step 3 of method B, 4. insert a fiberoptic scope through the diaphragm opening, into the mask, and optically guide the fiber optic scope by way of the nose or mouth into the trachea, force with lubrication, an endotracheal tube which was resident over the back portion of the fiberoptic scope, through the diaphragm opening, moving it in over the fiberoptic scope until it locates in the trachea, withdraw the fiber optic scope from the endotracheal tube, inflate the endotracheal tube cuff.
5. apply gas supply to the endotracheal tube and disconnect anesthesia circuit
6. slide the mask and adaptor back along the endotracheal tube to remove it from the face, and hang the mask and tube.

7-9. The alternate to hanging the mask is the same as above.

Method "A" poses the problem of cessation of gas supply to the patient during the time span necessary for steps 1 and 2. This forces the anesthesiologist to weigh the advantage of slow and deliberate work against expediting the procedure to minimize apenia time.

Method "B" carries the possibility of loss of anesthesia gas pressure through the surrounding space space between he fiberoptic scope and the endotracheal tube during intubation of the fiberoptic scope. Seal rings in the space to reduce gas loss restrict controlled movement between the tube and scope. Removing the mask from the patient's face after intubation causes physical stress on the endotracheal gas supply system as the mask is drawn to the back end of the tube.

Method "C" maintains a gas tight seal between the diaphragm and the fiberoptic scope during intubation of the scope, but limits the diameter of the endotracheal tube with respect to the diameter of the fiber optic scope. The diaphragm opening and resiliency of the diaphragm must be selected to accommodate the two diameters. Invariably fit with the diaphragm opening negatively affects at least one of gas tight seal, feel of the procedure, and freedom to advance the tube through the diaphragm. Removing the mask from the patient is also difficult and cumbersome.

One example of a mask with an opening incorporating a seal for a tube is an anesthesia mask described in U.S. Pat. No. 2,625,155, patented by A. E. Engelder on Jan. 13, 1953. The mask permits removal of accumulated secretions from the mouth and nose of the patient by suction through a catheter without need for lifting or removing the mask. A pair of nipples are provided on the side of the mask for gas lines. Two ports, a nasal port and an oral port, each with a removable plug, are located at the front of the mask. The nasal port is located below the center line of the mask for intubation through either nostril, and the oral port is located for access by the suction catheter to the root of the tongue. Each port is supplied with a rubber ring attached to the interior of the mask to provide a leakproof seal between the catheter and the mask. The catheter therefore may be left in place continuously during anesthesia, and aspiration may be a accomplished periodically by applying suction to the catheter.

Concord/Portex Company of Keene, N.H. 03431 offers a Y adaptor which attaches to a mask at an opening located on the mask for intubation. The Swivel Adaptor with fiberoptic Bronchoscopy cap, Part No. 04-625109 has a first opening for attaching to the mask, a second opening which swivels to allow the respiratory circuit to assume a convenient angle to reduce drag and uncomfortable pressure, and a third opening with a flexible diaphragm cap having a central opening therethrough for sealingly receiving a broncho-fiberscope. U.S. Pat. No. 4,475,548, patented by Muto on Oct. 9, 1984, describes a fitting for an adaptor that attaches to the back end of an endotracheal tube. It is suited for use after intubation of the endotracheal tube is completed. The fitting delivers a fiber optic tube or a suction catheter tube by way of the adaptor to the endotracheal tube. The adaptor includes a branch opening for attachment to a respirator circuit.

In order to maintain the desired pressure in the endotracheal tube that is attached to the adaptor, the fitting has a foam rubber body which is contained in a cylindrical head that tapers to a smaller diameter at its lower end that connects to the adaptor. A closely fitting cylindrical cap having an annular top defining a small central opening, is forced down over the head until the lower portion of the cap snap-locks over a ridge on the head. The foam rubber body, having a bell shape, and a volume that is greater than the enclosure formed by the capped head, is forced to simultaneously extend somewhat up through the central opening and down into the tapered smaller diameter.

In order to form a leak proof opening for delivery of the fiber optic tube to the adaptor and on into the endotracheal tube, a knife is inserted into the central opening and driven down through the foam forming a slit therethrough for receiving the fiber optic therethrough. Because the central opening is of smaller diameter than the inner diameter of the head, the slit does extend radially completely through the foam. When the slit is cut, the pressure in the foam is partially relieved locally at the cut near the annular so that the foam is slightly dimpled where it extends through the central opening.

In operation, the fitting is lubricated with a sterile saline solution on the foam body which is preferably made from open celled foam in order to retain the lubrication for an extended period. The fitting is then inserted by its lower end into the adaptor. The assembly is then connected to the ventilator circuit by way of the adaptor connection, and to the endotracheal tube by way of the adaptor connection for that purpose.

The fiberoptic scope or suction catheter is then inserted through the slit in the foam body, down through the adaptor, and and down through the tracheal tube with a complete seal at the fitting and no damage to the surface of the delicate optical fibers or other outer surface of the scope.

Different sizes of endoscopic tubes are accommodated due to the softness of the foam, more sizes than diaphragm wall apertures could accommodate. The open celled lubricated foam eases in-feed and withdrawal of tubes, more than with collar seals.

When endwise insertion of the fiberoptic scope tube is not possible, the fitting is made in two halves which snap together around the tube by means of pins and holes in ears which extend from the fitting cavity shell halves. This fixed compression arrangement and break through the fitting shell wall can reduce seal effectiveness.

The fitting, as pointed out earlier, is designed for attachment to an endotracheal tube assembly after intubation of the endotracheal tube. It would be difficult, however to use a unit of this type for a complete procedure of fiberoptic guided, endotracheal intubation.

The fitting must be either cut to perform method B, that is accommodate an endotracheal tube containing a fiberoptic scope, or cut to perform method C, that is accommodate a fiberoptic scope, then try to force through an endotracheal tube over the scope.

Either way, the problems associated with sealing rings and with diaphragms of the earlier apparatus for performing those methods apply with this one.

One adaptor which overcomes many of the problems associated with the above ring, diaphragm, foam body and other single stage seals is described in U.S. Pat. 4,580,556, patented by Kondur on Apr. 8, 1986.

It is a two stage apparatus, comprising a housing having three openings. The first opening is for attachment to an anesthesia mask. The second opening is for attachment to an anesthesia circuit. The third opening is for for receiving a stretchable diaphragm which snaps over the third opening by a rim around the third opening.

The housing receives an endotracheal tube through a central opening in the diaphragm, for intubation of the tube by way of the first opening and mask. A solid plug is provided for sealing the central opening in the absence of the endotracheal tube. The stretchable nature of the diaphragm allows endotracheal tubes of different diameter to be inserted through the opening.

A second plug of soft material fits in the back opening of the endotracheal tube. The second plug has a central throughbore and is flexible enough to receive a fiberscope fiberoptic tube or line therethrough for intubation of the fiberoptic tube by way of the endotracheal tube.

The diaphragm seals around the endotracheal tube which is passed down through the mask, while the second plug in the back of the endotracheal tube seals around the fiberscope that is passed down through the endotracheal tube.

As discussed earlier, a resilient opening of a diaphragm or plug limits the diameter of the tube that it can receive if a combination of good seal and low resistance to movement through the opening is to be maintained. Removal of the mask from the patient after intubation is difficult and cumbersome because the diaphragm seal must be drawn back along the endotracheal tube.

SUMMARY OF THE INVENTION

It is one object of the present invention to provide an adaptor for a mask, for endotracheal intubation under anesthesia of a line such as a fiberoptic tube or line, an endotracheal tube, or the like, for simplicity of explanation referred herein to as "tube".

It is another object of the invention to provide an adaptor for endotracheal intubation which seals around the tube, provides for adjustment of the sealing pressure upon the tube, and adjustment of resistance by the seal to movement of the tube through.

It is another object of the invention to provide an adaptor as above, further in which the seal can be removed from the tube, and in which the adaptor can be removed laterally over an enlarged back end of the tube.

It is another object of the invention to provide an adaptor as above, further in which a seal may be applied laterally to the tube, and in which seal pressure, and resistance to movement of the tube through the seal is adjustable.

It is another object of the invention to provide an adaptor as above which will receive just about any diameter tube commercially available for fiberoptic scopes, endotracheal tubes, catheters, and the like.

It is another object of the invention to provide an adaptor as above which can deliver anesthesia gas from an anesthesia circuit to the mask.

It is another object of the invention to provide an adaptor as above which can be quickly changed from accepting one tube diameter to another tube diameter, and provide an adjustable, slidable, seal around the tube.

Other objects and advantages will be apparent from the ensuing description of the invention.

In accordance with the invention, an adaptor includes a body having a passageway through the body, the body defining first and second openings to the passageway.

The first opening is for receiving a line means such as a fiberoptic line, an endotracheal tube, and the like, for advancing the line means by way of the passageway through the second opening, and through an anesthesia mask to a patient.

A seal core comprising compressible material, comprises two or more unitary sections which when assembled define a passageway through the seal core for sealing around the line means when the sections are assembled into the seal core.

The first opening includes a seat which is adapted for receiving the seal core so that a second end of the seal core passageway is in communication with the body passageway.

A head which includes an opening therethrough, includes a seat which is adapted for receiving the core so that a first end of the seal core passageway is in communication with the opening in the head. One of the seats includes an angled surface for engaging a bevel on the seal core.

Means are provided for moving the two seats toward one another for adjustably changing the distance between the two seats, for compressing the seal core for adjustably sealing the core around the line means.

Preferably, the diameter of the body passageway, the first opening, the second opening, and the opening in the head, each is greater than the diameter of the passageway through the seal core.

BRIEF DESCRIPTION OF THE DRAWINGS

In order that the invention be more fully comprehended, it will now be described, by way of example, with reference to the accompanying drawings, in which.

DESCRIPTION OF THE PREFERRED EMBODIMENTS

Before explaining the invention in detail, it is to be understood that the invention is not limited in its application to the detail of construction and arrangement of parts illustrated in the drawings since the invention is capable of other embodiments and of being practiced or carried out in various ways. It is also to be understood that the phraseology or terminology employed is for the purpose of description only and not of limitation.

Figure 1:
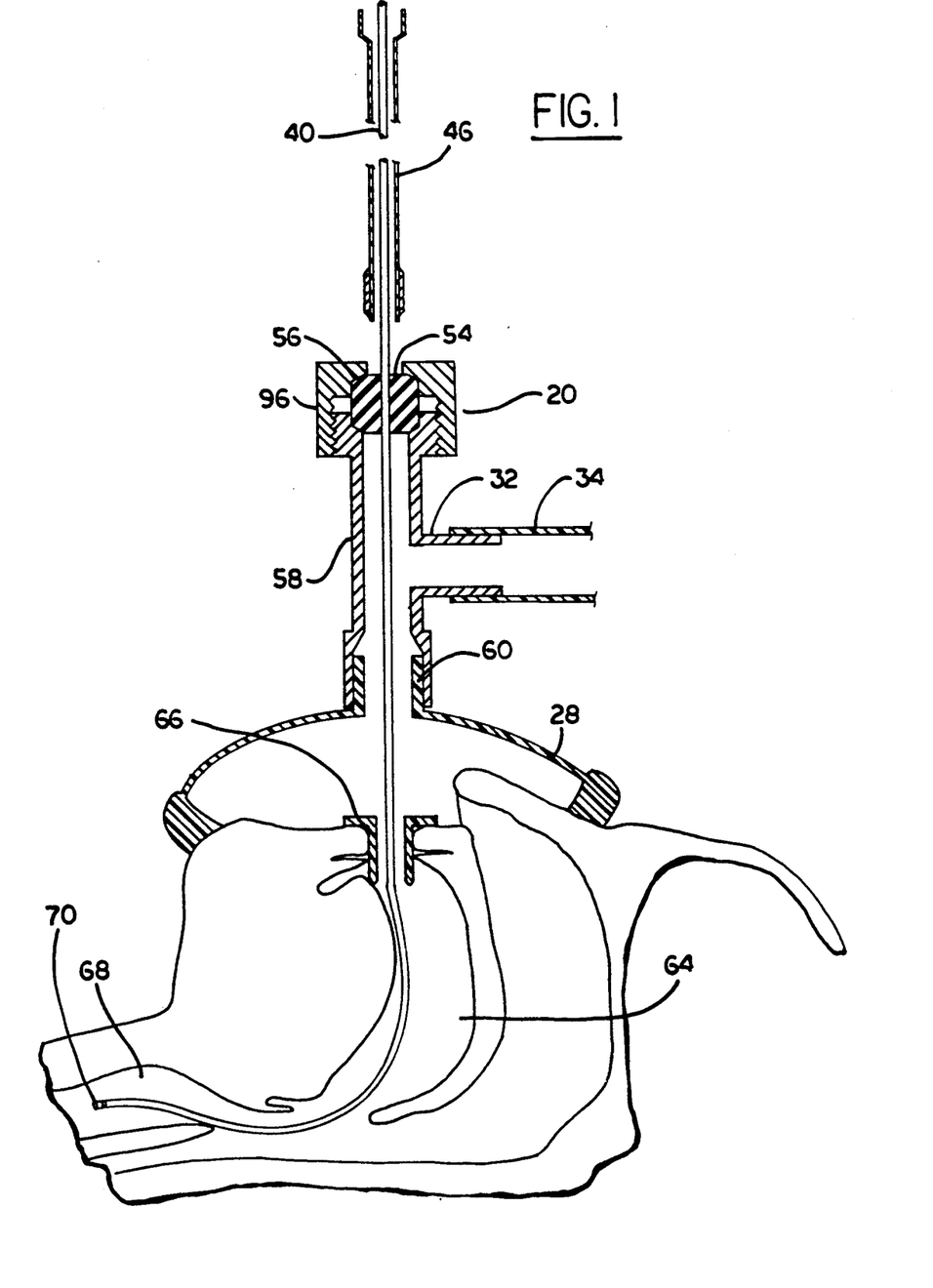
FIG. 1 is a cross section, schematic view of an adaptor according to the present invention, during intubation of a fiberoptic scope, prior to intubation of an endotracheal tube.

FIG. 1 shows an adaptor 20, according to a preferred embodiment of the invention, assembled with a mask, in a fiberoptic assisted endotracheal tube intubation procedure Adaptor 20, attached to anesthesia mask 28, is connected by side port 32 to an anesthesia circuit (not shown) by way of circuit tube 34.

Intubated fiberoptic scope tube 40, running thorough endotracheal tube 46, passes through split seal core 54 which is in core chamber 56 of adaptor body 58. Tube 46 continues on through anesthesia mask intubation port 60, intubating airway 66, and oral cavity 64, with tip 70 of the fiberoptic scope located in the trachea 68. This is an arrangement in a step prior to intubation of the endotracheal tube.

Figure 2:
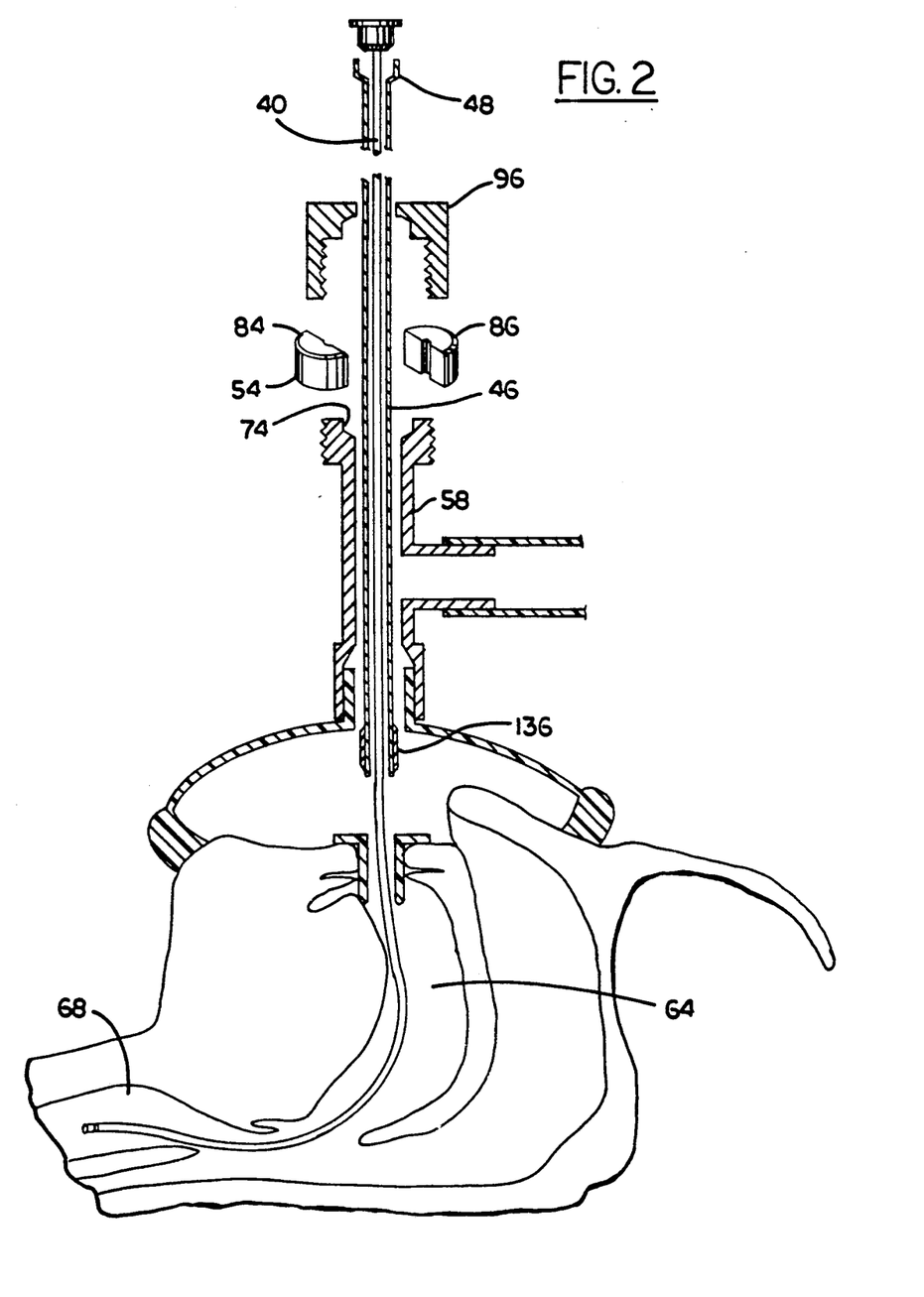
FIG. 2 is a cross section, partial perspective, schematic view of the adaptor of FIG. 1, with the fiberoptic scope seal removed for a quick intubation of the endotracheal tube.

FIG. 2 shows endotracheal tube 46 after it is slid over fiberoptic scope tube 40 which serves as a guide, and is moved past seal core chamber lower seat 74, on its way to the trachea as described earlier for methods A-C.

Adaptor 20 will now be described in detail with reference to FIGS. 3-6. Then an intubation method will be described with reference to FIGS. 7, 1, 2, 8, and 9.

Figure 3:
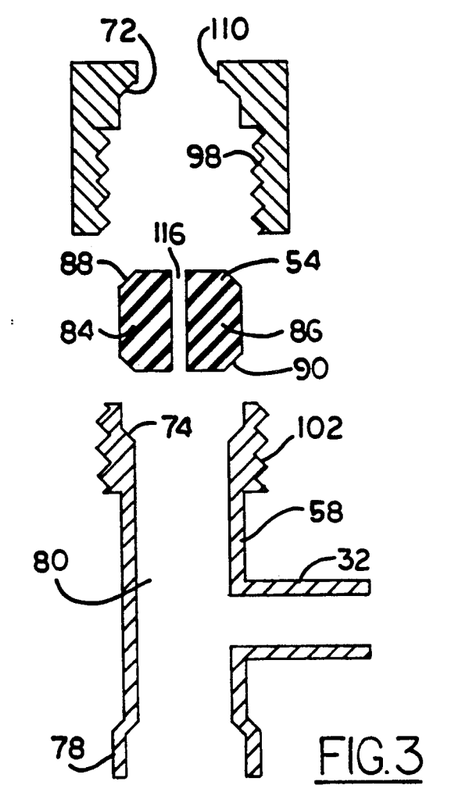
FIG. 3 is a cross section schematic view of an adaptor according to the present invention.

Turning now to FIG. 3, adaptor 20 body 58 is preferably made of a rigid, clear plastic for inspection of associated tubes and seals. It is hollow, with through opening 80 having an internal diameter that is sufficient to permit easy passage of gas and tubes. For example a minimum internal diameter through opening of 22mm would suffice.

The lower end of the body includes flared end 78 of suitable diameter opening, such as 26mm, and shape to fit a conventional anesthesia mask intubation port.

Seal core 54 is preferably made of transparent silicone rubber for inspection purpose, but may be made from opaque surgical rubber, foam rubber, or any surgical material that is compressible and fluid resistant. Preferably there is no interconnected porosity between the inner and outer surfaces of core 54.

Figure 5:
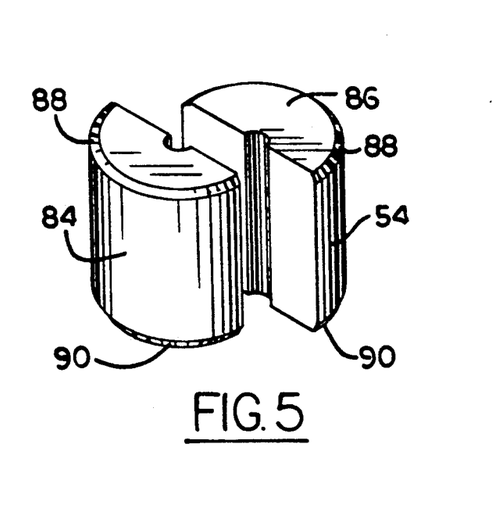
FIG. 5 is a perspective view of a seal according to the invention.

As shown in FIG. 5, the core comprises separable sections 84 and 86, which preferably are identical halves of the core. Top and bottom edge bevels 88 and 90 are preferably designed to closely fit seal core chamber upper angled seat 72 on threaded head 96 and lower angled seat 74 on body 58 (FIG. 3).

Threads 98 on head 96 match threads 92 on body 58.

Figure 4:
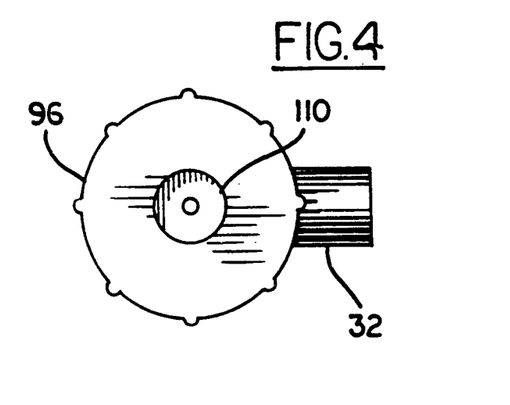
FIG. 4 is a top view of the adaptor shown in FIG. 3.

Referring to FIG. 4, knurls 106 on head 96 provide grip for screwing head 96 down on body 58. Opening 110 is large enough to pass over an enlarged opening at the rear end of an endotracheal tube, such as for enlarged end 48 of endotracheal tube 46 shown in FIG. 2. Central passageway 116 through seal core 54, between head opening 110 and through opening 80 in the body is formed by sections 84 and 86 when the sections are assembled into the unified element, core 54.

Figure 6:
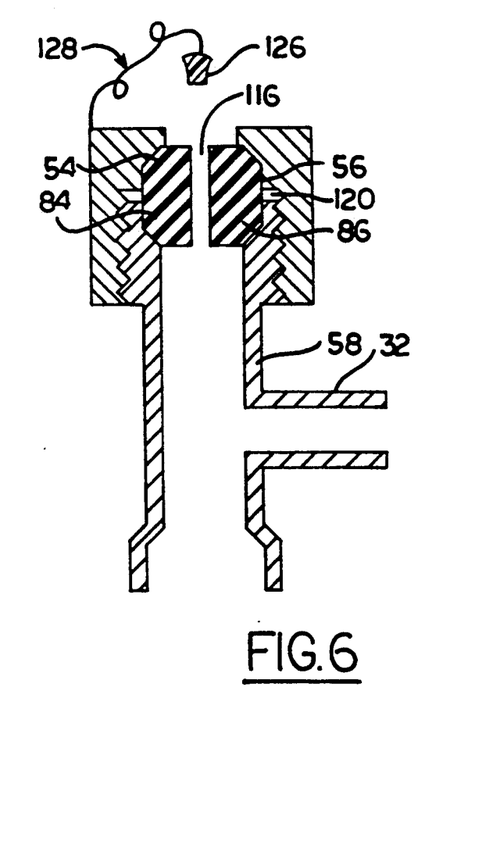
FIG. 6 is a cross section, schematic view of an adaptor according to the invention, assembled.

Referring to FIG. 6, head 96 is screwed down over body 58, forming seal core chamber 56 which encaptures seal core 54. Tightening head 58 by screwing it down over the body progressively compresses seal core 54 between the chamber upper and lower seats, reducing the diameter of passageway 116. The threads are of sufficient quantity, and pitch so that fine control of sealing pressure and sliding friction by seal core 54 on a tube in passageway 116 may be obtained by rotating head 96. Headspace 120 allows a wide compression latitude in order to accommodate a wide range of tube diameters.

When it is desired to control gas pressure in the body via side port 32, and passageway 116 is otherwise unoccupied, plug 126 on cord 128 is provided to seal the upper end of body by plugging passageway 116.

An intubation method according to the invention will now be described with reference to FIGS. 7, 1, 2, 8, and 9.

Figure 7:
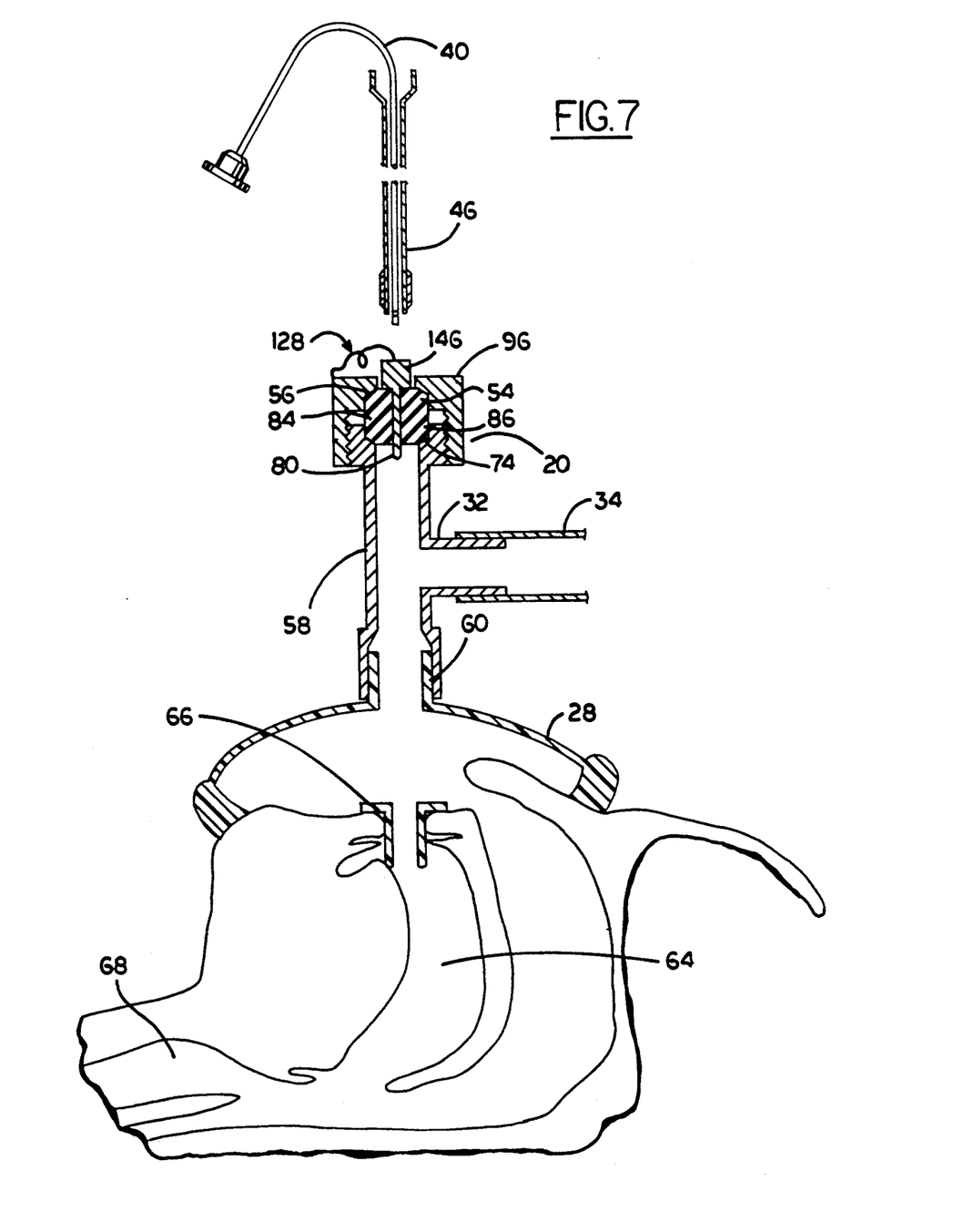
FIG. 7 is a cross section, partial perspective, schematic view of an adaptor according to the invention, attached to an anesthesia circuit during an intubation procedure.

In FIG. 7, intubating airway 65 and anesthesia mask 28 are in place on the patient. Through opening 80 is sealed by plug 146 in seal core 54 which was made from separable sections 84 and 86. Anesthesia pressure in the mask is thereby maintained until it is time to intubate fiberoptic scope tube 40.

Separable sections 84 and 86, seated in chamber seat 74 are selected so that recesses 132 and 134 which traverse the sections will form a passageway of suitable diameter in the assembled core that the passageway can be adjusted to seal around an inserted fiberscope tube 40 which is shown kept in the ready.

Head 96 is screwed down to adjust compression on seal core 54 by moving the upper and lower seats toward one another until seal core 54 provides an opening sufficient for slidably receiving fiberscope tube 40. This can be facilitated by having plug 126 at the approximate diameter of the fiberscope tube.

In FIG. 1, plug 146 is removed and fiberoptic scope tube 40, with endotracheal tube 46 on the rear end of tube 40 is inserted into seal core 54, with bottom end 130 of endotracheal tube 46 kept above head 96.

With a fluid tight, slidable seal maintained around tube 40, fine-adjusted by screwing head 96 if necessary, tube 40 is moved down until tip 70 is in the trachea. Bottom end 130 of endotracheal tube 46 remains above head 96.

In FIG. 2, the head is screwed up and sections 84 and 86 are separated to allow passage of endotracheal tube 46 on fiberoptic scope 40, into adaptor body 58, past seal core chamber lower seat 74. The tube may be advanced along the fiberoptic tube guide all the way to the trachea, wherein cuff 136 of the tube is expanded.

Figure 8:
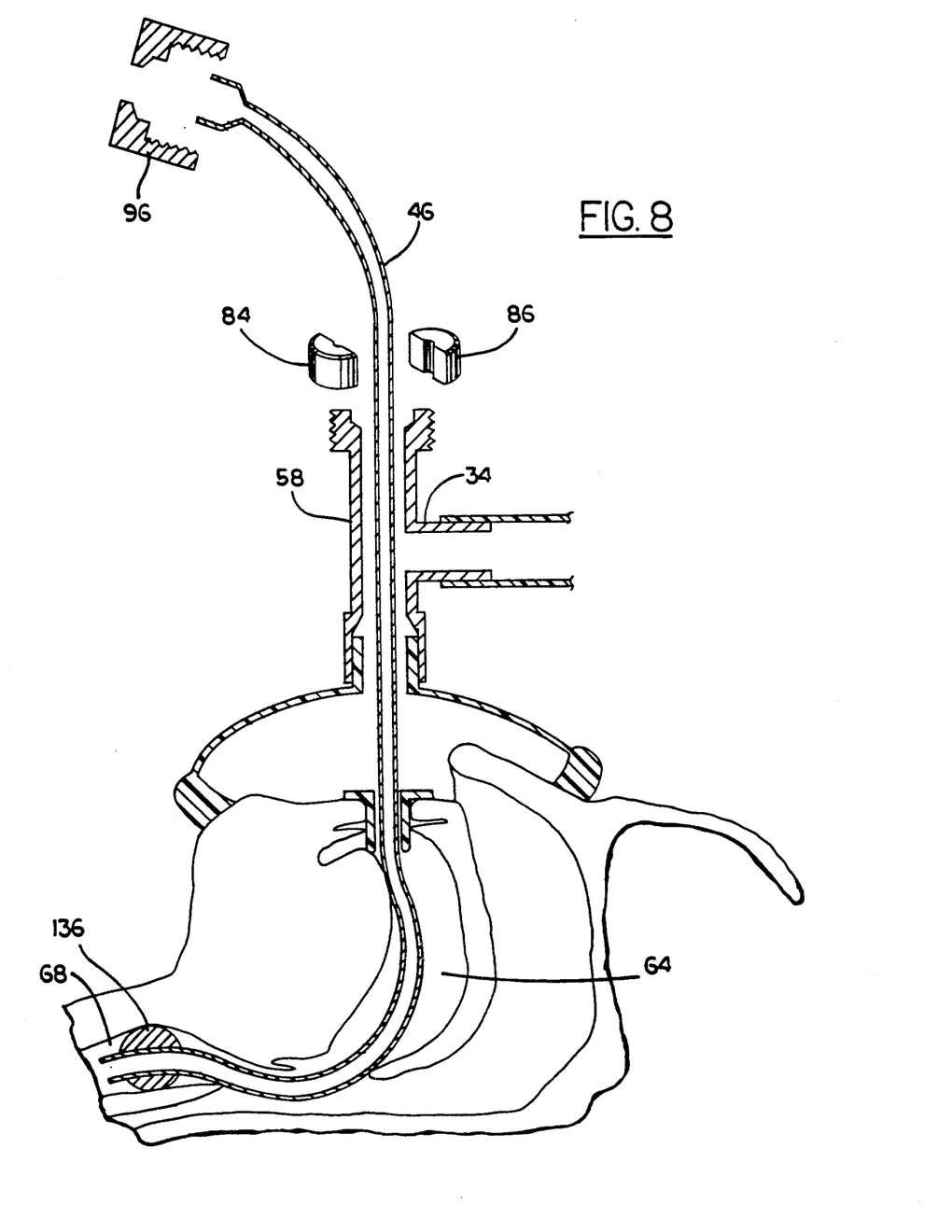
FIG. 8 is a cross section, partial perspective, schematic view of an adaptor according to the invention, attached to an anesthesia during an intubation procedure.

As shown in FIG. 8, the fiberoptic scope has been withdrawn from the endotracheal tube. Head 96 is screwed back off adaptor body 58, sections 84 and 86 are removed, and the head is removed from the endotracheal tube over the back end of the tube.

The anesthesia circuit is removed from circuit tube 34, and the adaptor body and mask are removed from the endotracheal tube over the back end of the tube.

The back end of the endotracheal tube is then attached to a gas supply in the conventional manner.

Figure 9:
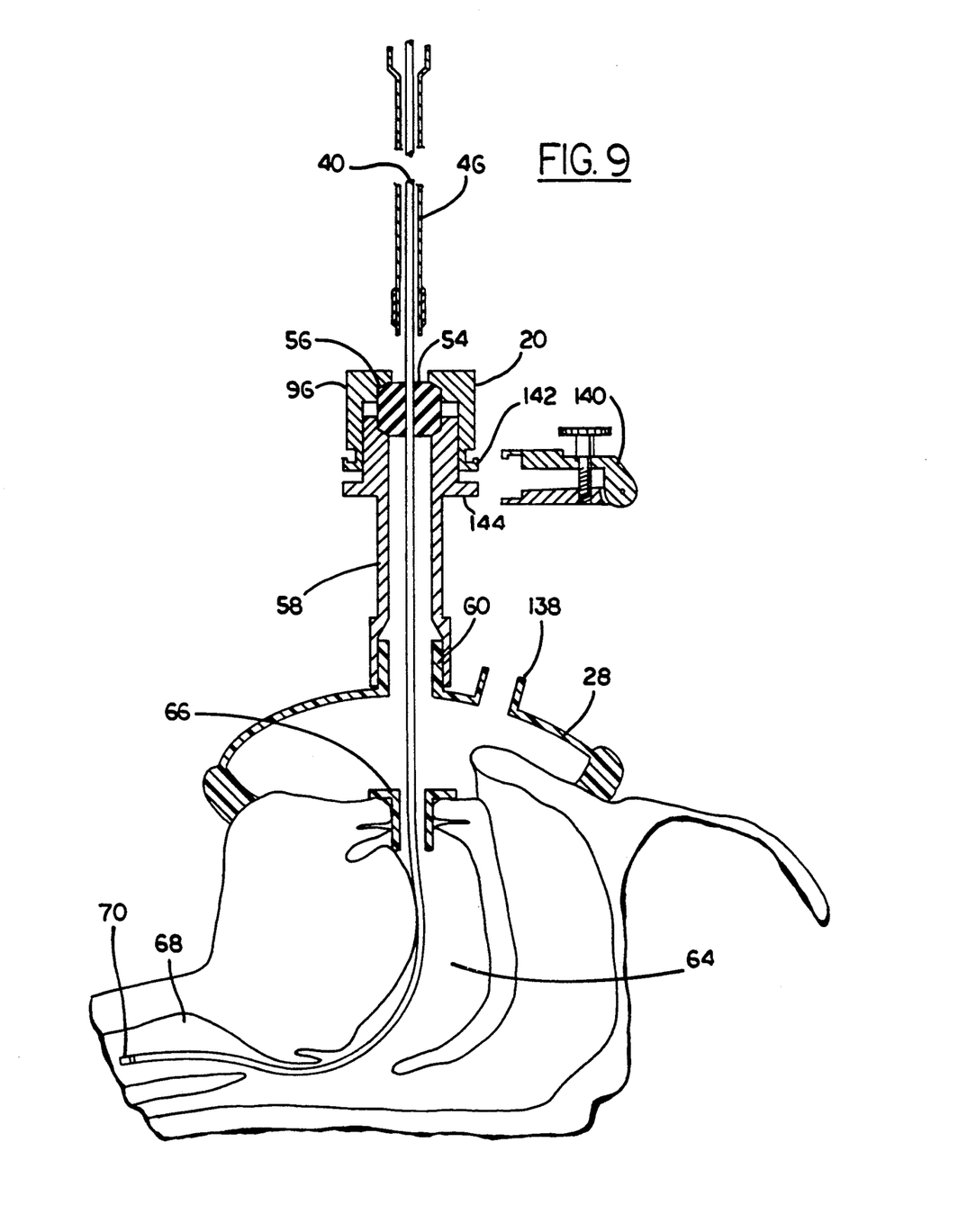
FIG. 9 is a schematic view of an adaptor according to the invention, attached to an anesthesia mask having an anesthesia circuit adaptor.

In the arrangement shown in FIG. 9, the above descriptions apply, except that the anesthesia circuit is connected to the mask directly by mask port 138, whereas in the earlier described arrangements, the anesthesia circuit is connected to the mask by way of side port 32 and adaptor body 58 through opening 80.

Although screw threads on the head and body are shown earlier for adjustably changing the distance between the seats, it is also within the contemplation of the invention to use any other adjustable means to adjustably move the seats toward one another such as, for example, external screws between the head and body, or a variably adjustable, slip-off clamp 140 between lips 142 and 144 on the head and body, as shown in FIG. 9.

Although the present invention has been described with respect to details of certain embodiments thereof, it is not intended that such details be limitations upon the scope of the invention. It will be obvious to those skilled in the art that various modifications and substitutions may be made without departing from the spirit and scope of the invention as set forth in the following claims.

What is claimed is:

1. An adaptor for use with an anesthesia mask for intubation of a patient by line means such as a fiberoptic line, an endotracheal tube, and the like, through said adaptor and said mask, said adaptor comprising:

a body comprising a first passageway from a first opening in said body, through said body, to a second opening in said body, said first opening being for receiving a line means for delivery to a patient by way of said passageway through said second opening and through a mask to said patient, and a seal core comprising a plurality of unitary sections which when assembled together about a common axis form said seal core and form a second passageway comprising a first end and a second end, through said seal core, said second passageway being for sealing around said line means when said sections are assembled into said seal core, said seal core comprising compressible material, said body's first opening comprising a first seat adapted for receiving said seal core so that said second end of said seal core's passageway is in communication with said body's passageway, a head including an opening through said head, adapted for joining with said body, said head comprising a second seat, said second seat being adapted for receiving said seal core so that said first end of said seal core's passageway is in communication with the opening through said head, and means for moving said first and second seats toward one another, for compressing said seal core for adjustably sealing said core around said line means.

2. The adaptor as described in claim 1, further comprising:

said means for moving said first and second seats toward one another comprising threads on aid body and mating threads on said head, said head being removable, and a one of said first and second seats comprising an angled surface for engaging a bevel on said seal core.

3. The adaptor described in claim 1, further comprising:

the first opening, second opening, and opening through said head, each being greater in diameter than the diameter of said second passageway.

4. The adaptor as described in claim 1, further comprising:

an anesthesia mask including means for attaching gas tubing directly to the mask for supplying gas to the patient.

5. The adaptor described in claim 1, further comprising:

a one of said first and second seats comprising an angled surface for engaging a bevel on said seal core, and a bevel on said seal core for said engaging of said angled surface.

* * * * *